United States Patent [19]
Spehr et al.

[11] Patent Number: 5,876,431
[45] Date of Patent: Mar. 2, 1999

[54] SMALL CABLE ENDOCARDIAL LEAD WITH EXPOSED GUIDE TUBE

[75] Inventors: Paul R. Spehr; James E. Machek, both of Lake Jackson, Tex.

[73] Assignee: Sulzer Intermedics Inc., Angleton, Tex.

[21] Appl. No.: 902,691

[22] Filed: Jul. 30, 1997

[51] Int. Cl.⁶ .................................................... A61N 1/05
[52] U.S. Cl. .......................................... 607/126; 607/127
[58] Field of Search .................................. 607/115, 116, 607/122, 125, 126, 127

[56] References Cited

U.S. PATENT DOCUMENTS

| | | | |
|---|---|---|---|
| 4,567,901 | 2/1986 | Harris | 128/786 |
| 4,716,888 | 1/1988 | Wesner | 607/126 |
| 4,919,135 | 4/1990 | Phillips, Jr. et al. | 607/126 |
| 5,129,404 | 7/1992 | Spehr et al. | 128/785 |
| 5,246,014 | 9/1993 | Williams et al. | 607/122 |

FOREIGN PATENT DOCUMENTS 306442 3/1989 European Pat. Off. .

OTHER PUBLICATIONS

Intermedics, Inc., Temporary Transcutaneous Pacing Wire Extension Lead Model 366–02—Sales Brochure, all pages, Oct. 1982.

CPI, Inc., *Endotak C Physicians's Manual*, all pages, date unknown.

*Primary Examiner*—William E. Kamm
*Assistant Examiner*—Carl H. Layno
*Attorney, Agent, or Firm*—John R. Merkling; Timothy M. Honeycutt

[57] ABSTRACT

A lead assembly adapted for endocardial fixation to a human heart is provided. The lead assembly includes a lead body that has a proximal end provided with a connector for electrical connection to a cardiac stimulator. The cardiac stimulator may be a pacemaker, a cardioverter/defibrillator, or a sensing instrument. The distal end of the lead body is connected to a tubular electrode housing. The lead body consists of a noncoiled conductor cable surrounded by a coextensive insulating sleeve. In contrast to conventional leads, the lead body of the present invention does not require coiled conductor wires or an internal lumen. Manipulation of the lead body is via an external guide tube. Lead body diameters of 0.25 mm or smaller are possible.

23 Claims, 6 Drawing Sheets

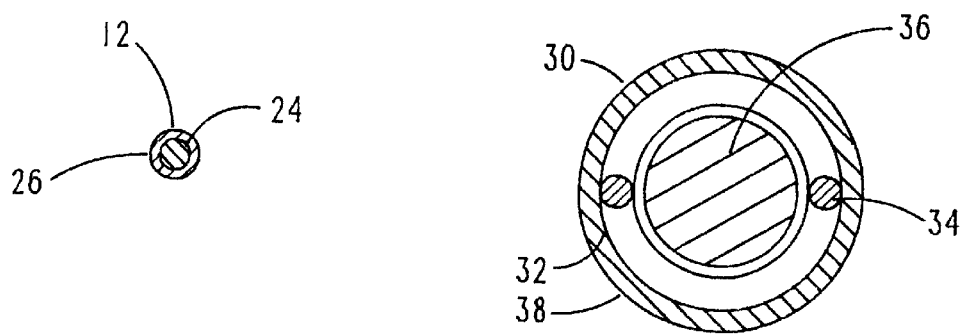
FIG. 3
(PRIOR ART)
FIG. 4
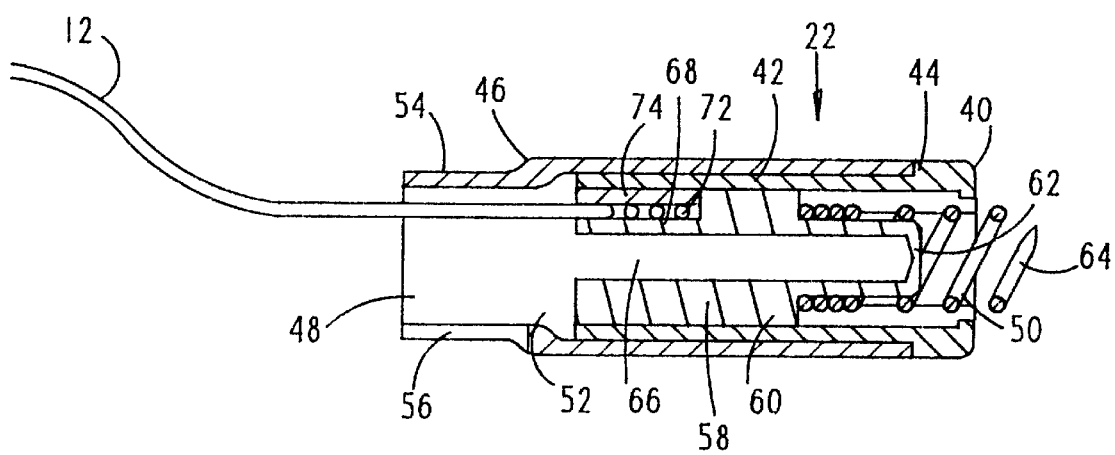
FIG. 5
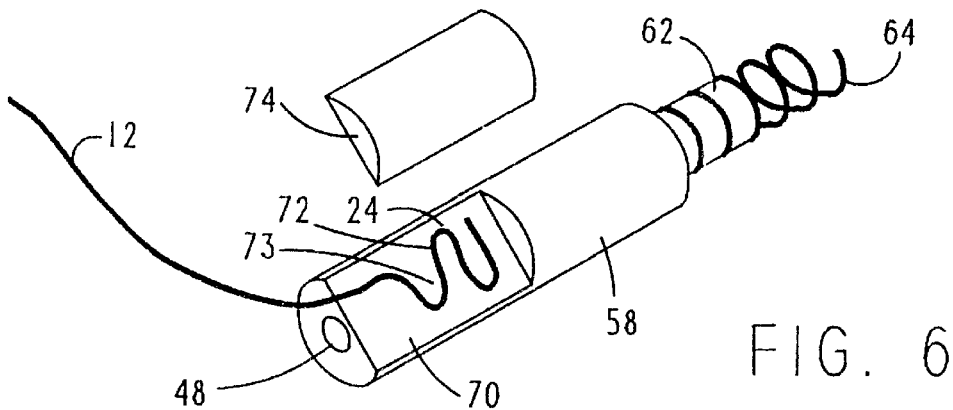
FIG. 6

SMALL CABLE ENDOCARDIAL LEAD WITH EXPOSED GUIDE TUBE

BACKGROUND OF THE INVENTION

1. Field of the Invention

This invention relates generally to cardiac stimulation leads, and more particularly to an implantable cardiac stimulation lead which employs a lead body encasing a very thin noncoiled conductor cable and an external guide tube.

2. Description of the Related Art

Prior to the advent of implantable endocardial stimulation leads, surgeons and cardiologists possessed few options for providing permanent or semi-permanent electrophysiological therapy to patients suffering from cardiac arrhythmia. In cases where drug therapy and corrective surgery were ruled out, epicardial leads used with external, and later implantable, pulse generators represented the normal clinical approach. For many patients whose arrhythmia stemmed from disruptions in electrical signal propagation at highly localized spots deep within the heart, epicardial stimulation constituted a compromise treatment.

The introduction of endocardial leads capable of transvenous implantation created a boon for many cardiac arrhythmia patients. Many individuals who formerly faced the prospects of median sternotomy or thoracotomy and reliance on epicardial stimulation for endocardially originated malfunctions could be provided with a subcutaneously implanted cardiac stimulator combined with a transvenous lead that promised to yield better cosmetic results as well as the potential for better therapy through more accurate placement of lead electrodes.

Despite the myriad of advantages associated with endocardial leads, there has always been a tradeoff associated with their usage in many patients. On the one hand, transvenous implantable leads typically yield better cosmetic results and the potential for more accurate arrhythmia therapy for patients. On the other, like any foreign body introduced into the cardiovascular system, a transvenous cardiac lead presents an obstruction to the normal flow of blood, and possibly the normal operation of one or more of the valves of the heart. This partial occlusion of a portion of the patient's cardiovascular system may result in not only a diminished blood flow, but also may lead to the formation of microemboli.

For the majority of patients, the medical advantages associated with endocardial leads strongly outweigh the attendant obstruction to normal blood flow. However, for some patients, the calculation is less clear. Pediatric patients often present blood vessels that are simply too small to accommodate conventional implantable leads, and these young patients are often the least able to adjust successfully to a diminished blood flow and/or valve function. Similarly, those patients who present occluded vessels and/or eroded valve leaves resulting from disease, injury, or some other mechanism may not be suitable candidates for transvenous implanted leads. In these types of cases, epicardial leads may present the only viable solution for the arrhythmia patient.

The magnitude of blood flow area of a given vessel obstructed by a conventional endocardial lead is a function of the diameter of the lead body. Early designs for endocardial leads consisted of an elongated lead body that included a proximal connector for connection to a pulse generator and a distally located electrode for transmitting signals to the heart. The lead body consisted of a tubular insulating sleeve that jacketed a coiled conductor wire leading from the electrode to the connector. The conductor wire was coiled in a helical fashion to leave a centrally disposed lumen through which a stylet could be inserted to manipulate the lead. The minimum overall diameter for this design is limited by the sum of the diameter of the lumen, twice the diameter of the conductor wire, and twice the wall thickness of the sleeve. An early bipolar variant incorporated two coiled conductor wires separately disposed in respective lumens. Here, the minimum diameter is a function of the sum of the diameters of both lumens, twice the diameter of the conductor wire, and twice the thickness of the sleeve. Diameters of 8 French (approximately 3 mm) (1 French=3×diameter in millimeters) were not uncommon.

Later lead designs incorporated a coaxial arrangement that represented an advance in miniaturization. The coaxial lead utilizes a lead body with an inner conductor wire defining a lumen, an outer conductor wire, an intermediary insulating sleeve separating the two conductor wires, and an outer insulating sleeve. The minimum diameter of the coaxial bipolar lead body is limited by the sum of the diameters of the lumen, the first conductor coil, the intermediary insulator sleeve, the second conductor coil, and the outer sleeve. Overall diameters of about 6 French (approximately 2 mm) are common with this design.

A recent improvement upon the coaxial bipolar design incorporates nested and individually insulated conductor wires that circumscribe a concentrically located lumen. This uniaxial design can be seen in the Thinline™ (a trademark of Sulzer Intermedics, Inc.) leads produced by Sulzer Intermedics, Inc. The diameter of the Thinline™ lead body is a function of the sum of the diameter of the lumen, the diameter of each of the conductor wires, and twice the wall thickness of the outer sleeve. The introduction of the Thinline™ lead design further reduced the minimum diameter of the lead body to about 4.7 French (approximately 1.6 mm).

Despite advances in miniaturization, there are still several disadvantages associated with conventional lead designs. Conventional lead bodies require an internal lumen that is coextensive with the lead body to accommodate an internal stylet for manipulating the lead. The diameter of the lumen often constitutes a significant portion of the overall diameter of the lead body and therefore represents a limitation on the achievable miniaturization of the lead body. Similarly, conventional lead bodies incorporate coiled conductor wires that, by definition, contribute twice their own diameters to the overall diameter of the lead body. For these reasons the smallest available conventional leads may still be too large for successful transvenous implantation in some patients.

In addition, coaxial leads are susceptible to structural failure due to a phenomenon commonly known as "subclavian crush." Subclavian crush occurs when a lead is implanted via the subclavian vein (a common transvenous entry site) and is pressed against the patient's clavicle during movement of the shoulder joint. The pressing force may bend the coils of the lead wire to fracture. The problem is exacerbated if the patient suffers an externally applied trauma in the clavicle area.

The present invention is directed to overcoming or minimizing one or more of the foregoing disadvantages.

SUMMARY OF THE INVENTION

In accordance with one aspect of the present invention, a lead assembly is provided. The lead assembly includes a tubular electrode housing that has a proximal end, a fixation mechanism, an electrode, and a pair of peripherally spaced longitudinally disposed slots. A lead body is provided that has a first end coupled to the proximal end of the tubular electrode housing, a second end, an elongated noncoiled conductor cable, and an insulative sleeve coating the noncoiled conductor cable. A connector is included that has a distal end coupled to the second end of the lead body for coupling to a cardiac stimulator. An elongated guide tube is provided that has a distal end removably engageable with the proximal end of the tubular electrode housing. The guide tube has a pair of peripherally spaced radially projecting keys to cooperatively engage the slots.

In accordance with another aspect of the present invention, a lead assembly is provided. The lead assembly includes connector for coupling to a cardiac stimulator and a lead body that has a first end coupled to the connector, a second end, an elongated noncoiled conductor cable, and an insulative sleeve coating the conductor cable. A tubular electrode housing is provided that has a proximal end coupled to the second end of the lead body, a fixation mechanism, an electrode, a pair of peripherally spaced longitudinally disposed slots, and a lumen extending through the tubular electrode housing. The lumen is eccentrically disposed relative to the second end of the conductor cable to enable the tubular electrode housing to slidably engage a stylet temporarily implanted to a desired location in advance of the lead assembly. An elongated guide tube is included that has a distal end removably engageable with the proximal end of the tubular electrode housing. The guide tube has a pair of peripherally spaced radially projecting keys to cooperatively engage the slots.

In accordance with still another aspect of the present invention, a lead assembly is provided. The lead assembly includes a connector for coupling to a cardiac stimulator and a lead body that has a first end coupled to the connector, a second end, an elongated noncoiled conductor cable, and an insulative sleeve coating the conductor cable. The lead body has a diameter smaller than about 4.7 French. A tubular electrode housing is provided that has a proximal end coupled to the second end of the lead body, a fixation mechanism, an electrode, a pair of peripherally spaced slots, and a lumen extending through the tubular electrode housing. The lumen is eccentrically disposed relative to the second end of the lead body to enable the tubular electrode housing to slidably engage a stylet temporarily implanted to a desired location in advance of the lead assembly. An elongated guide tube is provided that has a distal end removably engageable with the proximal end of the tubular electrode housing. The guide tube includes a pair of peripherally spaced radially projecting keys to cooperatively engage the slots.

BRIEF DESCRIPTION OF THE DRAWINGS

The foregoing and other advantages of the invention will become apparent upon reading the following detailed description and upon reference to the drawings in which:

FIG. 3 is the same view as FIG. 2 drawn approximately to a particular scale;

FIG. 4 is a cross-sectional view of a conventional Thinline™ lead body drawn to the same scale as FIG. 3;

FIG. 5 is a cross-sectional view of FIG. 1 taken at section 5—5;

FIG. 6 is an exploded pictorial view of a portion of the electrode housing depicted in FIG. 5 in accordance with the present invention;

DETAILED DESCRIPTION OF SPECIFIC EMBODIMENTS

Figure 1:
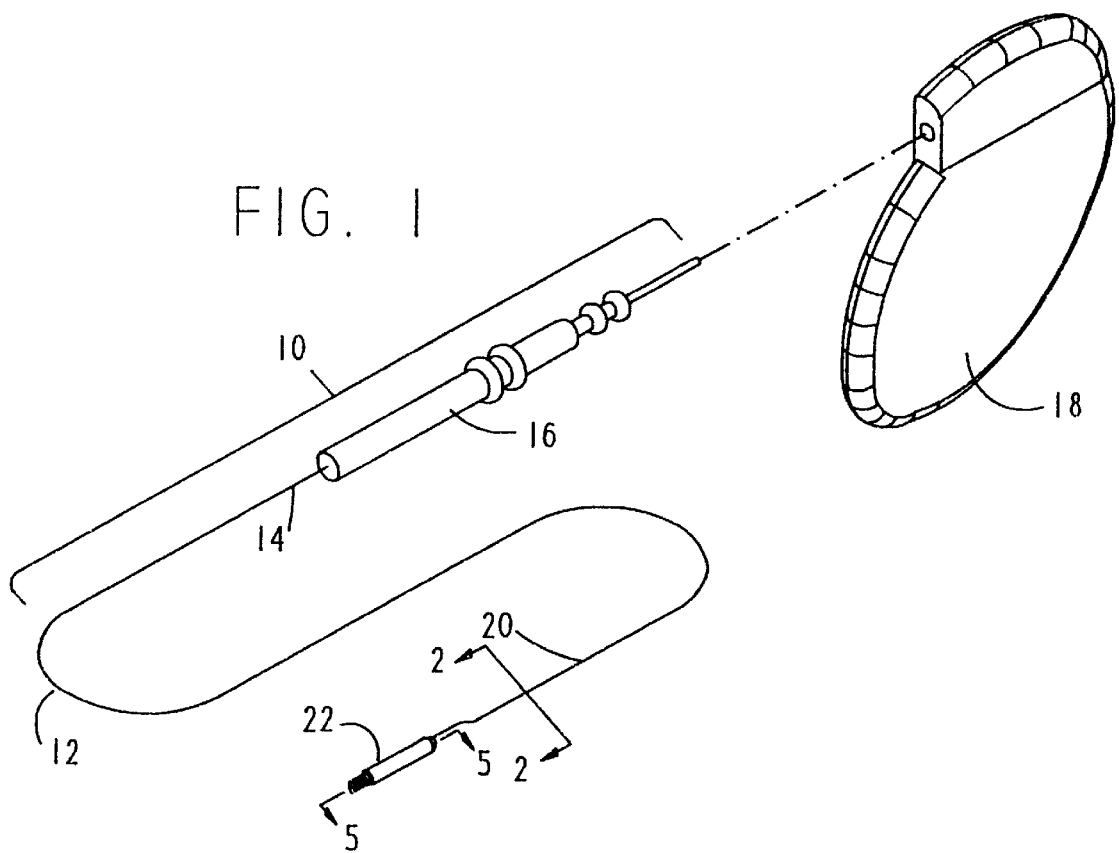
FIG. 1 is a pictorial view of an exemplary embodiment of a lead assembly in accordance with the present invention.
Figure 2:
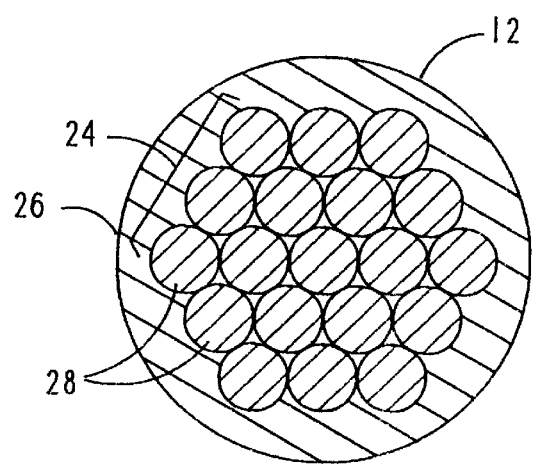
FIG. 2 is a cross-sectional view of FIG. 1 taken at section 2—2.

In the drawings described below, reference numerals are generally repeated where identical elements appear in more than one figure. Turning now to the drawings, and in particular to FIGS. 1 and 2, there is shown an exemplary lead assembly 10 that is adapted for endocardial fixation to a human heart. The lead assembly 10 includes a lead body 12 that has a proximal end 14 provided with a connector 16 for electrical connection to a cardiac stimulator 18. The cardiac stimulator 18 may be a pacemaker, a cardioverter/defibrillator, or a sensing instrument. The distal end 20 of the lead body 12 is connected to a tubular electrode housing 22. The proximal end 14 of the lead body 12 may be coupled to the connector 16 by conventional means such as crimping, laser, or spot welding.

FIG. 2 is a highly exaggerated cross sectional view of the lead body 12 taken at section 2—2. The view is exaggerated in scale because the actual diameter of the lead body 12 is only somewhat larger than a human hair. The lead body 12 consists of a conductor cable 24 surrounded by a coextensive insulating sleeve 26. The conductor cable 24 may be a single filament wire or a plurality of individual conductor wires 28 as shown The precise number and arrangement of the conductor wires 28 is a matter of design discretion. In the embodiment shown, the conductor cable 24 consists of nineteen individual metal conductor wires 28 having a combined diameter of approximately 0.127 mm. The insulating sleeve 26 has a wall thickness of approximately 0.0508 mm, making the total diameter of the lead body approximately 0.229 mm or 0.69 French. In contrast to conventional lead bodies, the conductor cable 24 is noncoiled, that is, not spiraled to define a concentrically disposed lumen. Consequently, the minimum diameter of the lead body 12 is limited only by the sum of the diameter of the cable 24 and twice the wall thickness of the sleeve 26.

The vivid contrast between the lead body 12 and a conventional 4.7 French diameter Thinline™ lead body can be readily seen in FIGS. 3 and 4, which show, respectively, side-by-side cross sectional views of the lead body 12 and a conventional Thinline™ lead body 30 both drawn to the same 1/32"=0.001" scale. FIGS. 3 and 4 show the relative size differences between the lead body 12 of the present invention and a conventional Thinline™ lead body 30. The conventional lead body 30 consists of coiled and nested conductor wires 32 and 34 defining a concentrically disposed lumen 36. The conductor wires 32 and 34 are surrounded by an insulating sleeve 38. The total diameter of the lead body 30 is a combination of twice the wall thickness of the sleeve 38, the combined diameters of the conductor wires 32 and 34, and the concentrically disposed lumen 36.

The conductor cable 24 is preferably manufactured from a biocompatible conducting material, such as, for example, MP35N alloy. MP35N alloy generally consists of a combination of cobalt, chromium, nickel, and molybdenum. A further discussion of the properties of MP35N alloy may be had by reference to U.S. Pat. Nos. 3,356,542 and 3,562,024. The lead body 12 should be capable of readily conforming to the irregular passageways and shapes of the cardiovascular system. Accordingly, the conductor cable 24 should have a high enough ductility to permit the lead body 12 to flex easily, and elastically. The conductor cable 24 is normally cold worked during fabrication. In the event the conductor cable 24 is composed of several individual wires 28, it is anticipated that the wires 28 should be slightly twisted to keep them together prior to the application of the sleeve 26. However, the wires 28 may have a tendency to resist the twist and spring apart due to the previous cold work. In this regard, the wires 28 may be heat set so that they do not unfurl prior to the application of the sleeve 26. A variety of heat setting protocols may be suitable. One possibility involves tempering at 600° F. for approximately one hour in an inert ambient, such as argon. The fully fabricated cable 24 may be obtained from the Xylem Company in Wayzata, Minn.

The insulating sleeve 26 is designed to provide biocompatible electrical insulation for the conductor cable 24 while providing an external surface that is smooth and does not promote microemboli. The sleeve 26 is preferably fabricated from a biocompatible polymer material, such as, for example, ETFE (fluoropolymer resin), or a similar biocompatible polymer material.

The detailed structure of the electrode housing 22 may be understood by reference to FIGS. 1 and 5. FIG. 5 is a cross sectional view of FIG. 1 taken at section 5—5. The electrode housing 22 includes a tubular electrode member 40 that has a proximally projecting reduced diameter portion 42 which defines a proximally projecting annular shoulder 44 located near the distal end of the tubular electrode member 40. The reduced diameter portion 42 is surrounded by an insulating sleeve 46 that is composed of a conventional biocompatible material such as polyurethane or silicone rubber. The distal end of the insulating sleeve 46 abuts against the annular shoulder 44. The proximal end of the insulating sleeve 46 includes an opening 48 and the distal end of the tubular electrode member 40 includes an opening 50. The interior surfaces of the tubular electrode member 40 and the insulating sleeve 46 as well as the openings 48 and 50 define a lumen 52. The proximal end of the insulating sleeve 46 includes a reduced diameter portion 54 that has a longitudinally disposed slot 56, the function of which is disclosed below.

A semi tubular plug 58 is disposed inside the tubular electrode member 40. The central portion 60 of the plug 58 includes a cylindrical surface that is sized to provide an interference fit with the interior surface of the tubular electrode member 40. The distal portion of the plug 58 includes a reduced diameter cylindrical tip 62. A fixation mechanism or corkscrew 64 is coiled around the exterior of the tip 62. The distal end of the corkscrew 64 projects from the opening 50 to provide active fixation to endocardial tissue. The plug 58 includes a lumen 66 that extends from the proximal end of the plug 58 to the distal end of the tip 62. However, note that the distal end of the tip 62 is closed. The lumen 66 is designed to receive a stylet under certain circumstances as discussed more fully below.

The upper side of the proximal portion of the plug 58, as viewed in FIG. 5, includes a cut-out 68, the structure and function of which may be understood by referring now also to FIG. 6, which is an exploded pictorial view of the plug 58 removed from the electrode housing 22. The horizontal surface 70 of the cut out 68 provides a platform upon which the distal end 72 of the lead body 12 may be secured. The distal end 72 of the lead body 12 is disposed on the horizontal surface 70 in a serpentine-like fashion. Most of the insulating sleeve 26 should be removed from the distal portion 72 to expose the conductor cable 24, though some portion of the sleeve 26 should be left on the distal end 72 in the vicinity of the proximal edge of the cut-out 68 to reduce the potential for short circuiting caused by body fluids. The particular configuration of the serpentine-like arrangement is a matter of discretion. However, care should be taken to provide the first bend 73 in the distal end 72 with a relatively large radius to reduce the potential for a stress riser.

A crimp block 74 is provided to secure the distal end 72 of the lead body 12 to the plug 58. The crimp block 74 is dimensioned to correspond to the cut out 68, and when pressed tightly on the cut-out 68 and over the distal end 72, acts as a crimping member to hold the distal end 72 in place as shown in FIG. 5. The crimp block 74 may be suitably dimensioned and/or the tubular electrode 40 may be swaged to provide an interference fit between the crimp block 74 and the interior surface of the reduced diameter portion 42 of the tubular electrode member 40. In addition to relying on friction to secure the lead body 12 to the electrode housing 22, the conductor cable 24 may also be spot or laser welded to the horizontal surface 70 to provide an additional attachment mechanism in the event the plug 58 is fabricated from a weldable material.

Figure 7:
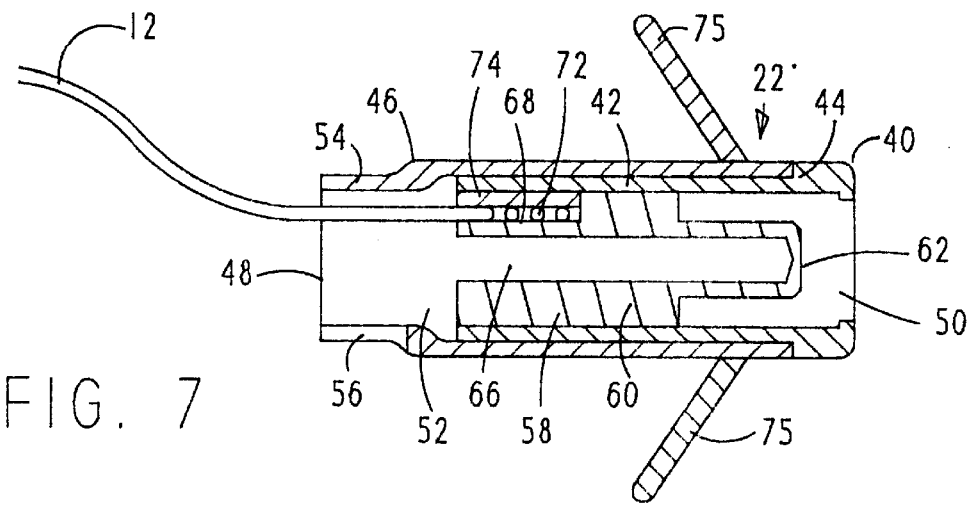
FIG. 7 is a cross-sectional view like FIG. 5 of an alternate embodiment of the electrode housing in accordance with the present invention.

The fixation mechanism or corkscrew 64 may be replaced by a passive fixation mechanism to secure the electrode housing 22 to endocardial tissue. FIG. 7 is a view of similar perspective to FIG. 5 and shows an embodiment of the electrode housing, now designated 22', that includes one or more outwardly projecting tines 75 that provide passive fixation. The number and arrangement of the tines 75 is a matter of design discretion. The tines 75 may be composed of a non-metallic biocompatible material, such as, for example, silicone rubber, polyurethane, polyethylene, polyimide, or similar materials.

The corkscrew 64 and the tubular electrode member 40 may be fabricated from a variety of biocompatible conducting materials, such as, for example, iridium oxide coated titanium. Other possible materials include MP35N, stainless steel, platinum-iridium alloy consisting of approximately 90% platinum and 10% iridium, or some other biocompatible conducting metal. The corkscrew 64 is preferably coated with a thin coating of an insulating polymer, such as Parylene C® supplied by Union Carbide, or a similar material. In general, the plug 58 and crimp block 74 may be fabricated from the same types of materials as the corkscrew 64, or may be composed of a non-metallic, biocompatible material, such as, for example, silicone rubber, polyurethane, polyethylene, polyimide, or similar materials. If the plug 58 is composed of a metallic material, the corkscrew 64 may be secured to the tip 62 by spot or laser welding. However, an electrical pathway must be established between the distal end 72 of the lead body 12 and the tubular electrode member 40. If the plug 58 is fabricated from a metallic material, this pathway is provided by the plug 58 itself. In this circumstance, the crimp block 74 need not be composed of a conducting material and may instead be fabricated from a variety of biocompatible, nonconducting materials, such as silicone rubber, polyurethane, polyethylene, polyimide, or similar materials. However, if the plug 58 is fabricated from a nonconducting material, the crimp block 74 should be fabricated from the same types of materials as the corkscrew 64 to establish the requisite electrical pathway from the distal end 72 to the tubular electrode member 40.

Figure 8:
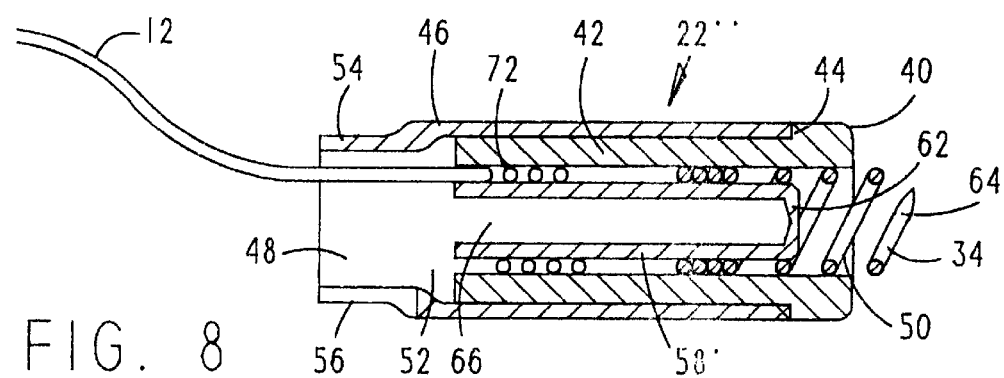
FIG. 8 is a cross-sectional view like FIG. 5 of another alternate embodiment of the electrode housing in accordance with the present invention.

The particular mechanism for securing the lead body 12 to the electrode housing 22 may take on a variety of configurations. For example, FIG. 8 shows an alternate embodiment of the electrode housing 22, now designated 22". In this embodiment, the plug 58 depicted in FIGS. 5 and 6 is replaced with a more streamlined plug 58' that is of relatively uniform diameter, and acts as a conventional crimp slug. The reduced diameter portion 42 of the tubular electrode member 40 is configured to serve as a crimp sleeve to secure the distal end 72. Note that in this embodiment, the distal end 72 is looped one or more times around the plug 58'. As in the foregoing embodiment, the distal end 72 may be laser or spot welded to the plug 58' prior to crimping by the tubular electrode member 40.

Figure 10:
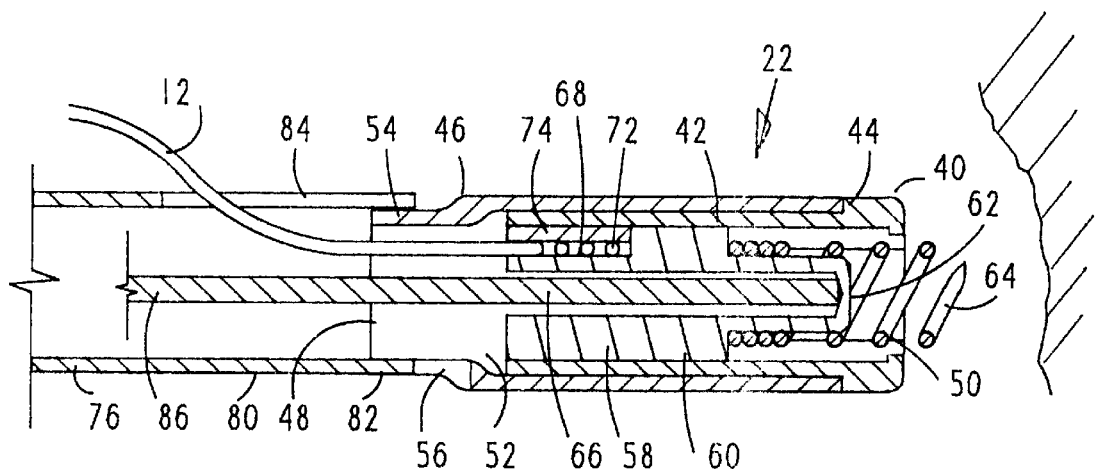
FIG. 10 is a cross-sectional view of FIG. 9 taken at section 10—10.
Figure 9:
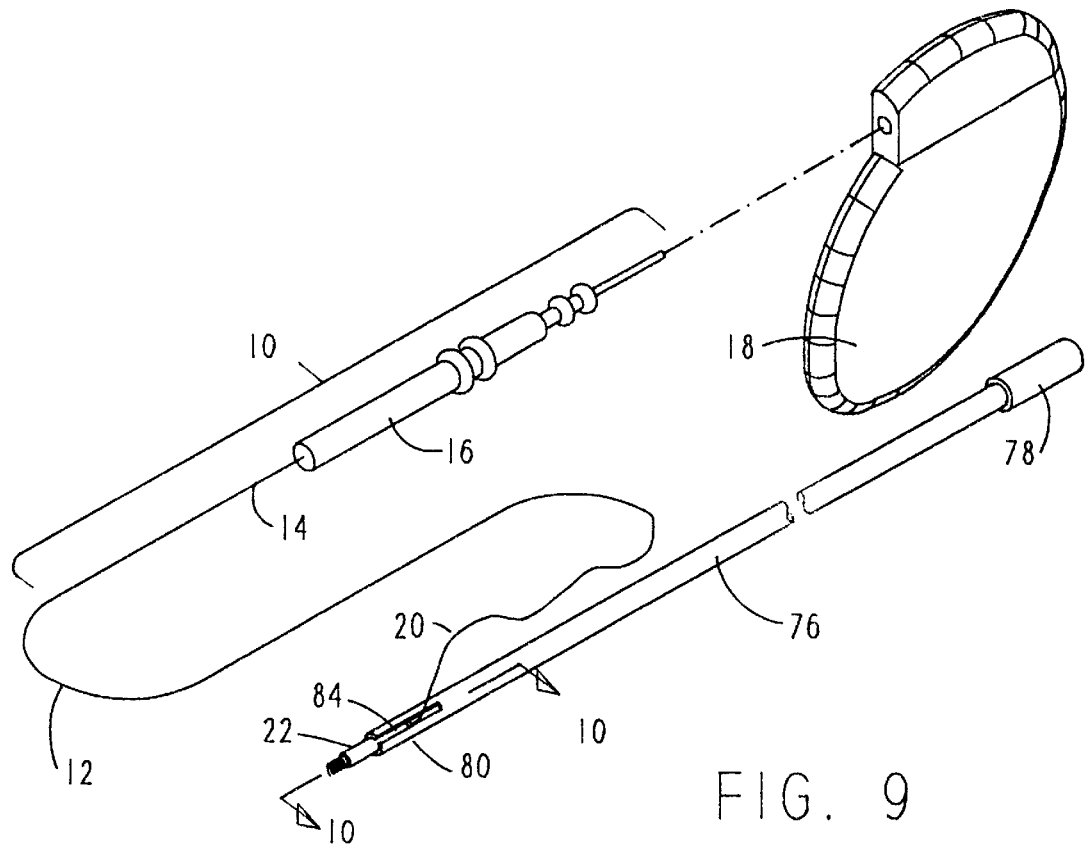
FIG. 9 is the pictorial view of FIG. 1 showing the placement of the guide tube in accordance with the present invention.

The manipulation of the lead assembly 10 during implantation or extraction may be understood by reference to FIGS. 9 and 10, which show, respectively, a pictorial view of the lead assembly 10 and a cross sectional view of FIG. 9 taken at section 10—10. A guide tube 76 may be slipped over the proximal end 54 of the electrode housing 22 to spatially manipulate the lead assembly 10. The guide tube 76 is provided with a proximally disposed handle 78 for manipulation of the guide tube 76 by hand. The distal end 80 of the guide tube 76 is provided with a longitudinally projecting key 82 that is configured to engage the slot 56 in the electrode housing 22. The engagement of the key 82 and the slot 56 enable a torque applied to the handle 78 to transmit into a rotational movement of the electrode housing 22, and in this way enable the corkscrew 64 to be twisted into the endocardium 83. The guide tube 76 does not require a key 82 if the electrode housing 22 utilizes passive fixation. The distal end 80 is also provided with a longitudinally aligned slot 84 that is peripherally displaced from the key 82. The presence of the slot 84 enables the guide tube 76 to be slipped over the reduced diameter portion 54 of the electrode housing 22 while maintaining the lead body 12 external to the guide tube 76. To prevent the guide tube 76 from slipping off of the electrode housing 22, the distal end 80 may be dimensioned to provide an interference fit with the reduced diameter portion 54 of the electrode housing 22, or tension may be maintained on the lead body 12 after the distal end 80 is slipped over the electrode housing 22 and until the electrode housing 22 is secured to the endocardium 83.

The guide tube 76 functions as a stylet. Accordingly, it is desirable for the guide tube 76 to be fabricated from a ductile material that may be readily plastically deformed by hand so that the surgeon can bend the guide tube 76 at various locations, as necessary, to place the electrode housing 22 at the desired location within the heart. Exemplary materials include nickel-titanium alloys commonly sold under the trade name Nitinol, polyurethane, polyethylene, and polyamide. These materials, and particularly Nitinol, are resistant to kinking.

To disengage the guide tube 76 from the electrode housing 22, a stylet 86 may be introduced into the guide tube 76 through the handle 78 and advanced into the lumen 66. The guide tube 76 and the electrode housing 22 may then be separated by simultaneously applying a thrust to the stylet 86 and a tensile force to the guide tube 76. The stylet 86 may then be withdrawn.

Figure 11:
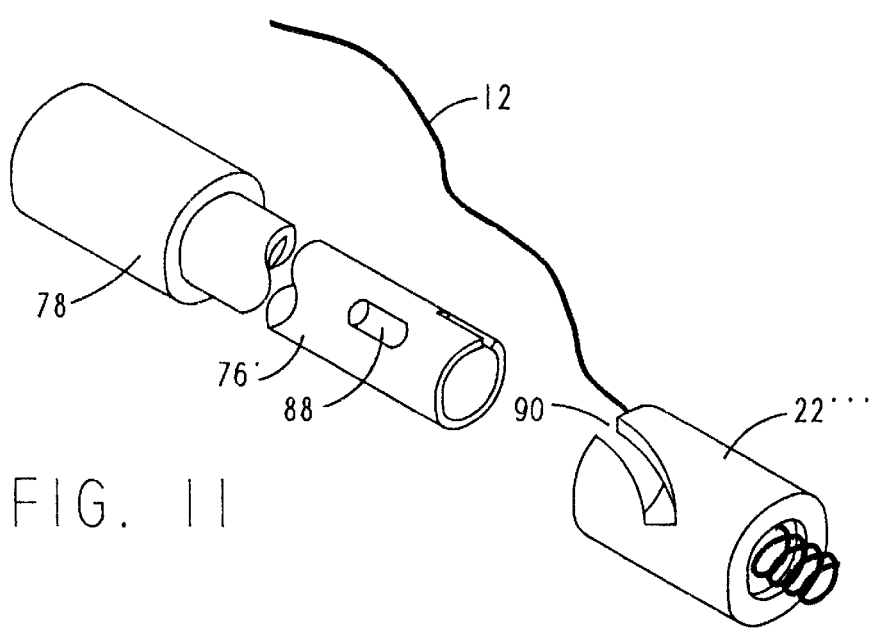
FIG. 11 is a pictorial view of an alternate embodiment of the guide tube shown in FIG. 9 in accordance with the present invention.
Figure 12:
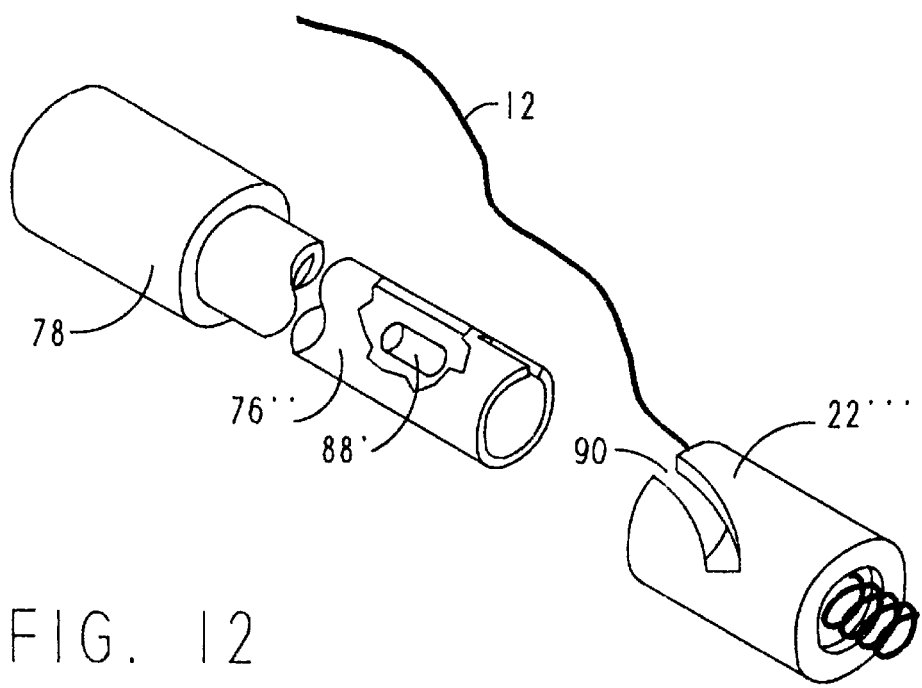
FIG. 12 is a pictorial view of another alternate embodiment of the guide tube shown in FIG. 9 in accordance with the present invention.

The particular mechanism for transmitting torque from the guide tube 76 to the electrode housing 22 may be varied. FIGS. 11 and 12 show, respectively, pictorial views of two such alternative configurations. In FIG.11, the guide tube, now designated 76', is provided with two diametrically opposed radially projecting cylindrical keys 88, only one of which is shown in FIG. 11. The electrode housing, now designated 22''', is provided with a pair of diametrically opposed arcuate slots 90, only one of which is shown in FIG. 11. The guide tube 76' is dimensioned to be slightly smaller in diameter than the electrode housing 22''' so that the guide tube 76' may be slipped into the proximal end of the electrode housing 22''' and advanced longitudinally with the keys 88 engaging the corresponding slots 90. The interaction of the keys 88 and the slots 90 enable transmission of torque from the guide tube 76' to the electrode housing 22". FIG. 12 shows another alternative configuration for the guide tube, now designated 76". In this embodiment, the keys, now designated 88', are disposed internal to the guide tube 76' and the guide tube 76" is dimensioned to be slightly larger in diameter than the electrode housing 22''' so that the guide tube 76" may be slipped over the exterior of the electrode housing 22''' and the keys 88 brought into sliding longitudinal engagement with the slots 90. Torque may then be transmitted from the guide tube 76" to the electrode housing 22'''. The keys 88 and 88' may be formed from the same materials used to fabricate the guide tubes 76 or 76" and may be integrally formed with the guide tubes 76 or 76" or fabricated as separate pins welded or press fit to the guide tube 76 or 76".

The implantation procedure of the lead assembly 10 may be understood by reference to FIGS. 9 and 10. The guide tube 76 is secured to the electrode housing as discussed above. The stylet 86 may also be inserted at this point. The electrode housing 22 is then introduced into one of the major veins leading to the heart, such as the subclavian vein or one of the internal jugular veins. Following initial transvenous entry, the electrode housing 22 is advanced by manipulation of the guide tube 76 and/or the stylet 86 until the electrode housing 22 is located at the desired point of fixation to the endocardium 83. If active fixation is employed, the surgeon may then twist the handle 78 to engage the cork screw 64 with the endocardium 83. If not, the surgeon need not twist the handle 78. In either case, the stylet 86 may then be used as necessary to disengage the guide tube 76 from the electrode housing 22. The guide tube 76, and the stylet 86, if used, may then be retracted and the connector 16 may then be connected to the cardiac stimulator 18. If the initial placement is unsatisfactory, the procedure may be reversed and repeated as often as necessary.

Figure 13:
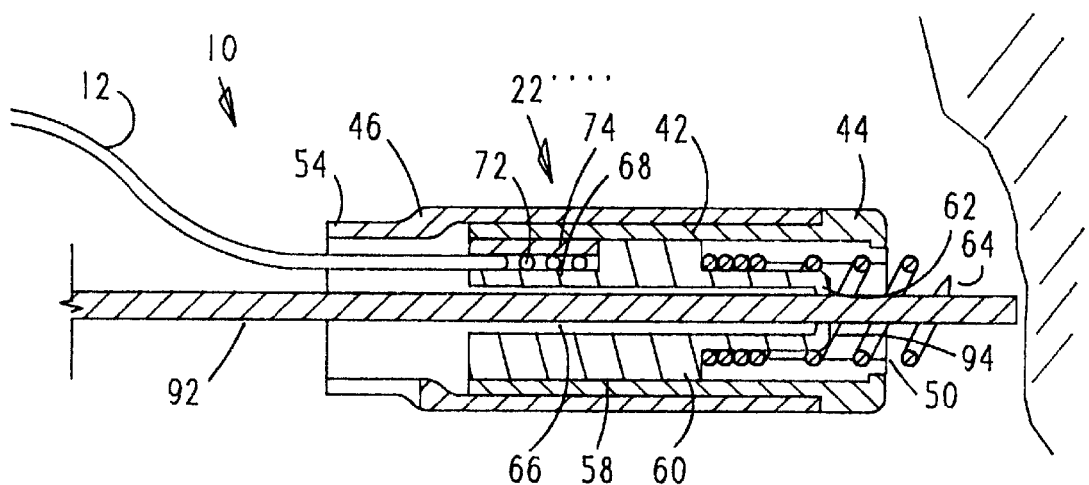
FIG. 13 is a cross-sectional view like FIG. 5 showing an alternate embodiment of the electrode housing configured to slide over a stylet in accordance with the present invention.

FIG. 13 is a partial sectional view of an alternate embodiment of the lead assembly 10 taken at the same general section as FIG. 5. In this embodiment, a particular pathway to the desired fixation point on the endocardium 83 is preestablished using a stylet 92. The tip 62 of the plug 58 is provided with an opening 94 so that the electrode housing, now designated 22'''', may be slipped over the proximal end of the stylet 92. Any of the guide tubes disclosed above may then be secured to the reduced diameter portion 54 of the electrode housing 22'''' and then, by manipulation of the guide tube 76, the electrode housing 22 may be advanced along the stylet 92 until the electrode housing 22'''' is disposed near the desired fixation point as shown in FIG. 13. The corkscrew 64 may then be secured to the endocardium 83 as disclosed above, either with the stylet 92 still in place or after the stylet 92 has been withdrawn. After the corkscrew 64 has been secured to the endocardium 83, the stylet 92 and the guide tube 76 (see FIG. 8) may be removed.

If the guide tube 76 is provided with an interference fit with the electrode housing 22, tension applied to the guide tube 76 to disengage it from the electrode housing 22 will be resisted only by the engagement of the corkscrew 64 with the endocardium 83. This may result in a disengagement of the corkscrew 64 with the endocardium 83. Accordingly, a stylet of the type shown in FIG. 8 but with a diameter sized to provide a slight interference fit with the lumen 66 may be inserted following removal of the stylet 92 to provide an opposing thrust against which tension applied to the guide tube 76 may act to achieve the desired disengagement. In this embodiment, the distal end 72 should be eccentrically disposed relative to the lumen 66 to avoid interfering with the movement of the electrode housing 22'''' along the stylet 92.

Figure 15:
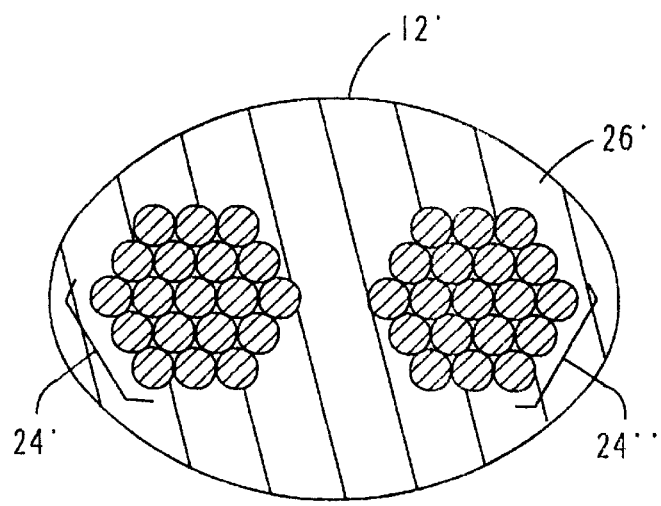
FIG. 15 is a cross-sectional view like FIG. 2 showing the lead body of FIG. 14 in accordance with the present invention.
Figure 14:
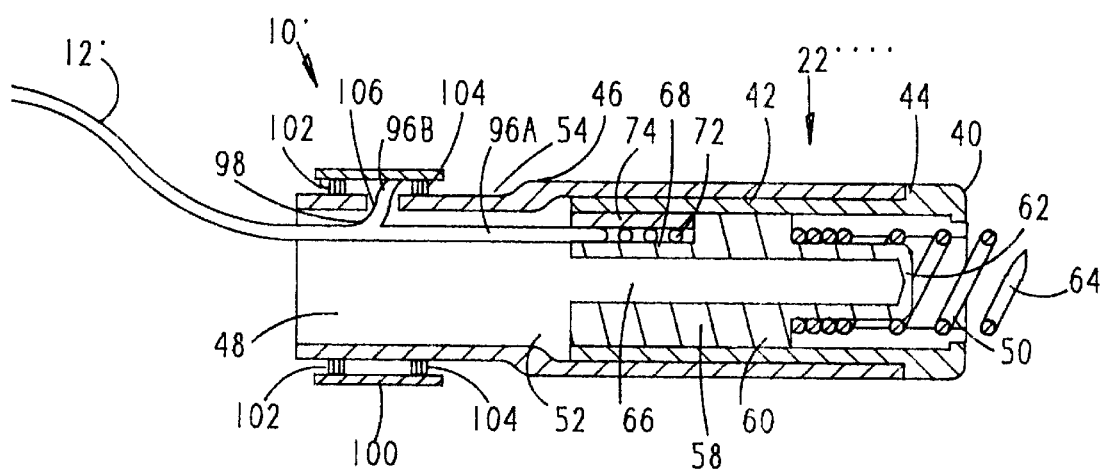
FIG. 14 is a cross-sectional view like FIG. 5 showing an alternate embodiment of the lead assembly that incorporates a bipolar lead body in accordance with the present invention.

The foregoing embodiments incorporate a unipolar lead body 12. However, multipolar lead bodies may be alternatively provided to facilitate multipolar stimulation and/or sensing. FIG. 14 is a cross-sectional view like FIG. 5 of an alternate embodiment of the lead assembly, now designated 10', which employs a bipolar lead body, now designated 12', The lead body 12' is bifurcated into two forks 96a and 96b at the branch 98. FIG. 15 is cross-sectional view of the lead body 12' taken proximal to the branch 98. As shown in FIG. 15, the lead body 12' includes two noncoiled conductor cables 24' and 24'' disposed in a parallel relationship and surrounded by an insulating sleeve 26'. Distal to the branch 98, each of the cables 24' and 24'' is individually covered by a portion of the sleeve 26' and is similar in cross-section to the lead body 12 shown in FIG. 5. The branch 98 may be formed by severing the sleeve 26' between the cables 24' and 24'' or by separately jacketing the distal ends of the cables 24' and 24'' at the time the lead body 12' is fabricated. The sleeve 26' and the cables 24' and 24'' may be fabricated from the materials disclosed above.

The branch 96a is coupled to the electrode housing, now designated 22''''', in the manner described above for coupling the lead body 12. The other branch 96b is connected to a second annular electrode 100 that is disposed over the sleeve 46' proximal to the electrode housing 22'''''. The sleeve 46' is elongated proximally to accommodate the electrode 100. Two annular members 102 and 104 are disposed between the sleeve 46' and the second electrode 100. To establish electrical connection between the branch 96b and the electrode 100, the branch 96b is projected through an opening 106 in the sleeve 46' located in that portion of the sleeve 46' covered by the annular electrode 100. The distal end of the branch 96b is stripped to expose the bare cable 24''. The bare cable 24'' is sandwiched between the exterior of the annular member 104 and the interior of the annular electrode 100. Prior to installing the annular electrode 100, the bare cable 24'' is secured to the annular member 104 by laser or spot welding. After the cable 24'' is secured to the annular member 104, the annular electrode 100 is positioned and swaged. The swaging serves to reduce the diameter of the annular electrode 100 and to ensure physical contact between the annular electrode 100 and the cable 24'' and/or the annular member 104.

The skilled artisan will appreciate that several electrodes may be incorporated into the lead assembly 10' and serviced by a corresponding plurality of noncoiled cables disposed in a parallel relationship. The overall diameter of such a lead body will be significantly smaller than a conventional lead body. Regardless of the number of cables in the lead body 12', the implantation procedure will be the same as disclosed above.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A lead assembly, comprising:
   a tubular electrode housing having a proximal end, a fixation mechanism, an electrode, and a pair of peripherally spaced longitudinally disposed slots;
   a lead body having a first end coupled to the proximal end of the tubular electrode housing, a second end, an elongated noncoiled conductor cable, and an insulative sleeve coating the noncoiled conductor cable;
   a connector having a distal end coupled to the second end of the lead body for coupling to a cardiac stimulator; and
   an elongated guide tube having a distal end removably engageable with the proximal end of the tubular electrode housing, the guide tube having a pair of peripherally spaced radially projecting keys to cooperatively engage the slots.

2. The lead assembly of claim 1, wherein the lead body has a second noncoiled conductor cable disposed in parallel relation to the first noncoiled conductor cable, the second noncoiled conductor cable having a second electrode couple thereto.

3. The lead assembly of claim 1, wherein the lead body has diameter smaller than about 4.7 French.

4. The lead assembly of claim 1, wherein the fixation mechanism comprises a corkscrew.

5. The lead assembly of claim 1, wherein the fixation mechanism comprises a tine projecting outwardly from the tubular electrode housing.

6. The lead assembly of claim 1, wherein the guide tube is composed of Nitinol.

7. The lead assembly of claim 1, wherein the keys project radially outwardly from the exterior surface of the guide tube.

8. The lead assembly of claim 1, wherein the keys project radially into the interior of the guide tube.

9. The lead assembly of claim 1, wherein the tubular electrode housing has a lumen extending therethrough and being eccentrically disposed relative to the first end of the conductor cable to enable the tubular electrode housing to slidably engage a removable stylet temporarily implanted to a desired location in advance of the lead assembly.

10. A lead assembly, comprising:
    a connector for coupling to a cardiac stimulator;
    a lead body having a first end coupled to the connector, a second end, an elongated noncoiled conductor cable, and an insulative sleeve coating the conductor cable;

a tubular electrode housing having a proximal end coupled to the second end of the conductor cable, a fixation mechanism, an electrode, a pair of peripherally spaced longitudinally disposed slots, and a lumen extending through the tubular electrode housing, the lumen being eccentrically disposed relative to the second end of the lead body to enable the tubular electrode housing to slidably engage a stylet temporarily implanted to a desired location in advance of the lead assembly; and an elongated guide tube having a distal end removably engageable with the proximal end of the tubular electrode housing, the guide tube having a pair of peripherally spaced radially projecting keys to cooperatively engage the slots.

11. The lead assembly of claim 10, wherein the lead body has a second noncoiled conductor cable disposed in parallel relation to the first noncoiled conductor cable, the second noncoiled conductor cable having a second electrode couple thereto.

12. The lead assembly of claim 10, wherein the lead body has a diameter smaller than about 4.7 French.

13. The lead assembly of claim 10, wherein the fixation mechanism comprises a corkscrew.

14. The lead assembly of claim 10, wherein the fixation mechanism comprises a tine projecting outwardly from the tubular electrode housing.

15. The lead assembly of claim 10, wherein the keys project radially outwardly from the exterior surface of the guide tube.

16. The lead assembly of claim 10, wherein the keys project radially into the interior of the guide tube.

17. The lead assembly of claim 10, wherein the guide tube is composed of Nitinol.

18. A lead assembly, comprising:

a connector for coupling to a cardiac stimulator;

a lead body having a first end coupled to the connector, a second end, an elongated noncoiled conductor cable, and an insulative sleeve coating the conductor cable, the lead body having a diameter smaller than about 4.7 French;

a tubular electrode housing having a proximal end coupled to the second end of the conductor cable, a fixation mechanism, an electrode, a pair of peripherally spaced slots, and a lumen extending through the tubular electrode housing, the lumen being eccentrically disposed relative to the second end of the lead body to enable the tubular electrode housing to slidably engage a stylet temporarily implanted to a desired location in advance of the lead assembly ; and an elongated guide tube composed of Nitinol and having a distal end removably engageable with the proximal end of the tubular electrode housing, the guide tube having a pair of peripherally spaced radially projecting keys to cooperatively engage the slots.

19. The lead assembly of claim 18, wherein the lead body has a second noncoiled conductor cable disposed in parallel relation to the first noncoiled conductor cable, the second noncoiled conductor cable having a second electrode couple thereto.

20. The lead assembly of claim 18, wherein the fixation mechanism comprises a corkscrew.

21. The lead assembly of claim 18, wherein the fixation mechanism comprises a tine projecting outwardly from the tubular electrode housing.

22. The lead assembly of claim 18, wherein the keys project radially outwardly from the exterior surface of the guide tube.

23. The lead assembly of claim 18, wherein the keys project radially into the interior of the guide tube.

* * * * *